United States Patent [19]

Maignan et al.

[11] Patent Number: 5,158,977
[45] Date of Patent: Oct. 27, 1992

[54] COSMETIC AND PHARMACEUTICAL COMPOSITIONS CONTAINING NAPHTHALENOL DERIVATIVES

[75] Inventors: Jean Maignan, Tremblay les Gonesse; Gérard Malle, Villiers sur Morin; André Deflandre, Orry-la-Ville; Gérard Lang, Saint Gratien, all of France

[73] Assignee: L'Oreal, Paris, France

[21] Appl. No.: 711,883

[22] Filed: Jun. 7, 1991

Related U.S. Application Data

[62] Division of Ser. No. 535,202, Jun. 8, 1990, Pat. No. 5,043,482.

[30] Foreign Application Priority Data

Jun. 13, 1989 [FR] France ............... 89 07805

[51] Int. Cl.$^5$ ............................. A61K 31/19
[52] U.S. Cl. ........................ 514/569; 514/682; 514/718; 514/720; 514/732; 514/887; 514/970
[58] Field of Search .............. 514/569, 682, 718, 720, 514/732, 887, 970

[56] References Cited

U.S. PATENT DOCUMENTS 3,426,358  2/1969  Schlichting ................ 568/736
4,156,789  5/1979  Hauck et al. ............... 568/736

Primary Examiner—Leonard Schenkman
Attorney, Agent, or Firm—Cushman, Darby & Cushman

[57] ABSTRACT

A 5,6,7,8-tetrahydro-1-naphthalenol derivative of the formula

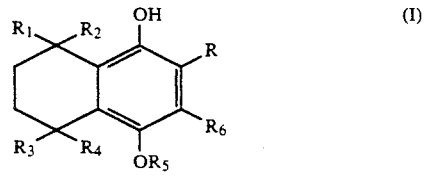

wherein
$R_1$, $R_2$, $R_3$ and $R_4$ represent lower alkyl,
$R_5$ and $R_6$ represent hydrogen or lower alkyl,
R represents hydrogen, $C_1$–$C_{18}$ alkyl, $C_2$–$C_{18}$ alkyl substituted by one or more hydroxyl groups, $C_3$–$C_{18}$ alkenyl, $C_2$–$C_{18}$ acyl, benzyl, benzoyl, carboxyl and carboxylic salts of an alkali or alkaline earth metal or of an organic amine.

The derivative is useful as an antioxidant in cosmetic compositions and in pharmaceutical compositions for the preventive treatment of cutaneous inflammations and allergies or certain forms of cancer.

9 Claims, No Drawings

COSMETIC AND PHARMACEUTICAL COMPOSITIONS CONTAINING NAPHTHALENOL DERIVATIVES

This is a division of application Ser. No. 07/535,202, filed Jun. 8, 1990 now U.S. Pat. No. 5,043,482.

The present invention relates to new derivatives of 5,6,7,8-tetrahydro-1-naphthalenol, a process for their preparation and their use as antioxidants in cosmetic compositions and in pharmaceutical compositions for the preventative treatment of cutaneous inflammations and allergies or certain forms of cancer.

The new derivatives of 5,6,7,8-tetrahydro-1-naphthalenol, in accordance with the present invention, are considered to exhibit in a surprising fashion excellent antioxidant properties vis-a-vis the peroxidation of polyunsaturated lipids and also vis-a-vis substances susceptible of undergoing to thermo or photo-induced oxidation reactions (such as protein, sugars, pigments, vitamins, polymers and the like).

Now, it is known that the peroxidation of lipids implies the formation of intermediary free radicals which damage cellular membranes composed of among others, phospholipids and are responsible principally for the phenomenon of skin ageing (A. L. Tappel in "Federation Proceedings", Vol. 32, No. 8, August, 1973).

Because of their antioxidant properties, the new derivatives of 5,6,7,8-tetrahydro-1-naphthalenol of the present invention provide an improved means for combatting premature ageing of the skin caused by peroxidation of cutaneous lipids.

They also assure a better preservation of cosmetic or pharmaceutical compositions containing an oily phase by avoiding the rancidity of unsaturated lipids which are present therein and which can be of animal origin such as lanolin, cetin (spermaceti), beeswax, perhydrosqualene and turtle oil, or of vegetable origin such as olive oil, ricin oil, corn oil, sweet almond oil, avocado oil, karite oil, turnsol oil, soy oil, peanut oil, copra oil, hydrogenated palm oil, essential fatty acids such as vitamin F and certain essential acids present in perfumes such as lemon oil or lavender oil.

These new derivatives also permit the avoidance of the oxidative degradation of active compounds contained in pharmaceutical compositions (vitamin A, carotenoids and the like).

In a quite surprising manner, it has also been noted that the 5,6,7,8-tetrahydro-1-naphthalenol derivatives, in accordance with the present invention, can also be employed in the treatment of cutaneous inflammations and allergies and also in the prevention of certain cancers.

In addition to their good antioxidant properties, the new derivatives of 5,6,7,8-tetrahydro-1-naphthalenol exhibit excellent liposoluble characteristics as well as very good thermal stability. Moreover, they also exhibit the advantage of being non-toxic or non-irritating and have perfect innocuousness vis-a-vis the skin.

These new derivatives of 5,6,7,8-tetrahydro-1-naphthalenol can be represented by the following general formula

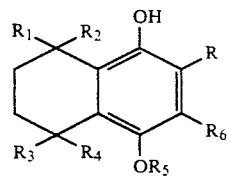

wherein
$R_1$, $R_2$, $R_3$ and $R_4$ represent lower alkyl,
$R_5$ and $R_6$ represent hydrogen or lower alkyl,
R represents hydrogen, $C_1$-$C_{18}$ alkyl, $C_1$-$C_{18}$ alkyl substituted by one or more hydroxy groups, $C_3$-$C_{18}$ alkenyl, $C_2$-$C_{18}$ acyl, benzyl, benzoyl, carboxyl and carboxylic salts of an alkali or alkaline earth metal or of an organic amine.

By lower alkyl is meant a radical having 1-6 carbon atoms.

Representative lower alkyl radicals and those having up to 18 carbon atoms, include principally methyl, ethyl, isopropyl, isobutyl, butyl, tert. butyl, 2-ethylhexyl, isooctyl, dodecyl, hexadecyl and octadecyl radicals.

Representative $C_1$-$C_{18}$ alkyl radicals substituted by one or more hydroxyl groups, include principally the 1-hydroxyethyl, 2-hydroxypropyl, 1-hydroxypropyl, 1-hydroxybutyl, 1-hydroxyhexyl, 1-hydroxy-1-ethylhexyl or 2,3-dihydroxypropyl radicals.

Representative $C_3$-$C_{18}$ alkenyl radicals include principally propenyl, butenyl, hexenyl, octenyl, dodecenyl and octadecenyl radicals.

Representative $C_2$-$C_{18}$ acyl radicals include principally acetyl, propionyl, butyryl, isobutyryl, hexanoyl, octanoyl, dodecanoyl and octadecanoyl radicals.

When R is benzyl or benzoyl it can be represented by the following formula

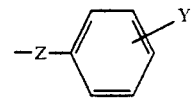

wherein
Z represents —CO—, —CHOH— or —CH$_2$— and
Y represents hydrogen, halogen and preferably chlorine, alkoxy and preferably methoxy or trifluoromethyl.

The salts of the compounds of formula I when R=—COOH are preferably salts of sodium, potassium, magnesium or an organic amine such as triethanolamine.

Representative particularly preferred derivatives of 5,6,7,8-tetrahydro-1-naphthalenol corresponding to general formula I include particularly the following:
4-methoxy-5,5,8,8-tetramethyl-5,6,7,8-tetrahydro-1-naphthalenol,
2-acetyl-4-methoxy-5,5,8,8-tetramethyl-5,6,7,8-tetrahydro-1-naphthalenol,
2-(1-hydroxyethyl)-4-methoxy-5,5,8,8-tetramethyl-5,6,7,8-tetrahydro-1-naphthalenol,
2-(2-hydroxy-2-propyl)-4-methoxy-5,5,8,8-tetramethyl-5,6,7,8-tetrahydro-1-naphthalenol,
2-(2-propenyl)-4-methoxy-5,5,8,8-tetramethyl-5,6,7,8-tetrahydro-1-naphthalenol,
1-hydroxy-4-methoxy-5,5,8,8-tetramethyl-5,6,7,8-tetrahydro-1-naphthalene carboxylic acid, 1,4-dihydroxy-5,5,8,8-tetramethyl-5,6,7,8-tetrahydro-1-naphthalene, 2-benzoyl-4-methoxy-5,5,8,8-tetramethyl-5,6,7,8-tetrahydro-1-naphthalenol and 2-benzyl-4-methoxy-5,5,8,8-tetramethyl-5,6,7,8-tetrahydro-1-naphthalenol.

The present invention also relates to a process for preparing the compounds of formula I such as defined above.

This process can be represented by the following reaction scheme

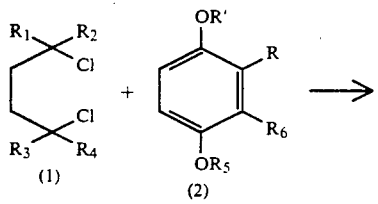

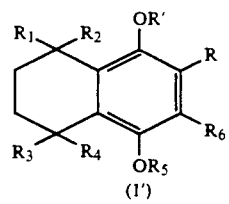

R' = H or alkyl

It consists essentially in reacting a 2,5-dichloro alkane (1) with a 4-alkoxy phenol (2) (R'=H) or a 1,4-dialkoxy benzene (2) (R'=alkyl) in an organic solvent such as nitromethane or a dichloro solvent such as 1,2-dichloroethane or methylene chloride, but preferably 1,2-dichloroethane, in the presence of a Lewis acid, preferably aluminum chloride. This reaction is, however, only possible when the nature of the substituents R and $R_6$ permit it.

When the initial reactant (2) is a 1,4-dialkoxy benzene, the 1,4-dialkoxy derivative of formula (1') (R'=alkyl) is then submitted to a treatment in the presence of hydriodic or hydrobromic acid to produce the corresponding phenol (I') (R'=H).

In accordance with a preferred embodiment, the compounds of formula (I) in which R=H are obtained starting with compounds of formula (1') wherein R=H and this in accordance with the following reaction scheme:

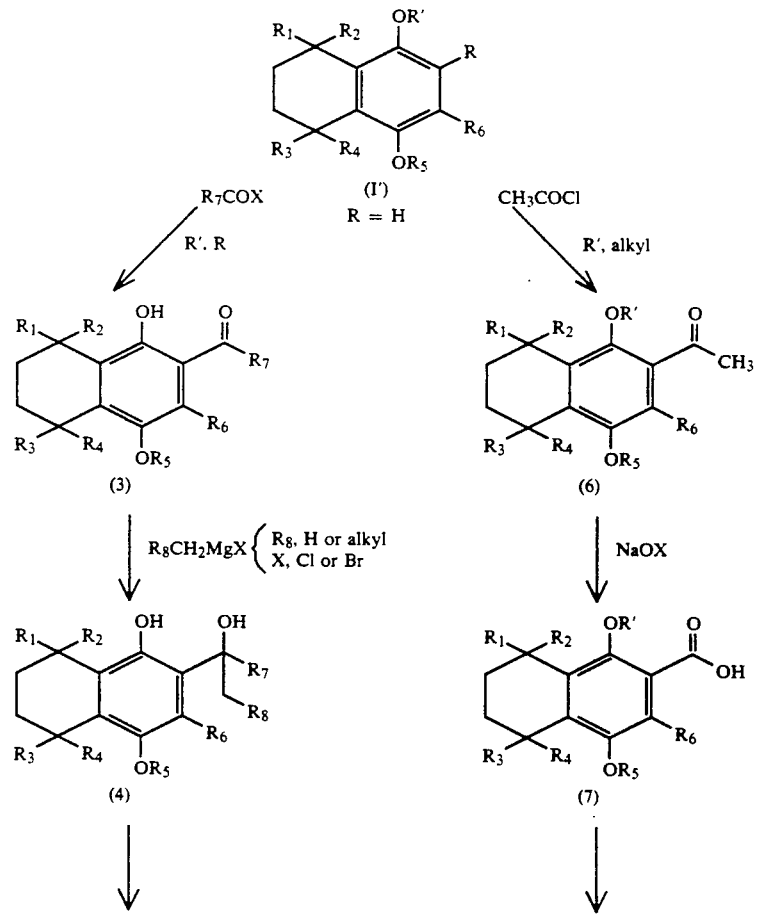

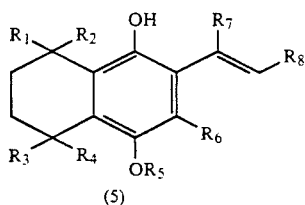

(5)

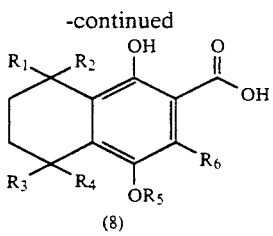

(8)

By acylation of the compound of formula (I') wherein R and R'=H using an acid halide or an acid anhydride in the presence of aluminum chloride, the ketone of formula (3) is obtained in a very good yield.

This ketone (3) can be reduced by sodium borohydride into the corresponding alcohol in a solvent such as methanol or ethanol or in an ether such as tetrahydrofuran or in a mixture of these solvents.

The ketone (3) can also be transformed into a tertiary alcohol (4) by the direct action of a magnesium alkyl halide under classic conditions for organo-magnesium reactions.

This tertiary alcohol (4) treated in an acid medium leads to the corresponding alkene (5) in a good yield.

The compound of formula (I') wherein R=H and R'=alkyl can be acylated by the action of acetyl chloride in the presence of aluminum chloride so as to produce the ketone (6).

This can then be transformed by oxidation with sodium hypochlorite or hypobromite into the corresponding acid (7).

This acid (7) treated by hydriodic or hydrobromic acid in an organic acid such as acetic acid leads then to the acid (8).

According to the duration of the treatment with hydriodic or hydrobromic acid, this acid (8) must be purified because it contains either the remainder of the initial reactant (7), or a hydroquinone derivative (compound of formula 8 in which $R_5$=H).

The present invention also relates to a cosmetic composition comprising, in a cosmetically acceptable support containing at least one fatty phase, an effective amount of at least one 5,6,7,8-tetrahydro-1-naphthalenol derivative of formula (I) such as defined above.

The cosmetic composition of the present invention can be employed as protective composition of human skin or hair or as an anti-sola composition.

In accordance with the invention the compound of formula (I) is generally present in an amount ranging from 0.05 to 10 weight percent relative to the total weight of the cosmetic composition and preferably from 0.1 to 5 weight percent.

In the compositions according to the present invention, the compound of formula (I) acts as an antioxidant agent. These compositions can be capillary compositions such as hair lacquers, hair setting lotions or hair treating or disentangling lotions, shampoos, coloring shampoos, hair dye compositions, makeup products such as nail enamels, skin treating creams and oils, foundations, lipsticks, compositions for the care of the skin such as bath oils or creams as well as any other cosmetic composition capable of exhibiting, because of their components, oxidation stability problems during storage.

As has been stated above, the compounds of formula (I) also exhibit an interesting pharmacologic activity in the field of the preventative treatment of cutaneous inflammations and allergies. They can also be employed in the prevention of certain cancers.

The present invention thus relates to a compound of formula (I) in its use as a medicine.

The present invention also relates to a pharmaceutical composition, containing an effective amount of at least one compound of formula (I) as an active ingredient in a non-toxic support or excipient.

The pharmaceutical composition conforming to the present invention can be administered orally or topically.

When administered orally, the pharmaceutical composition can be provided in the form of tablets, gelules, lozenges, syrups, suspensions, solutions, emulsions and the like.

When administered topically, the pharmaceutical composition of the present invention can be provided in the form of ointments, creams, pomades, solutions, lotions, gels, sprays, suspensions and the like.

These medicinal compositions can contain inert or pharmacodynamically active additives an principally hydrating agents, antibiotics, steroidal or non-steroidal anti-inflammatory agents, carotenoids or anti-psoriasic agents.

This composition can also contain flavor improving agents, preservatives, stabilizing agents, humidity regulating agents, pH regulating agents, osmotic pressure modifying agents, emulsifiers, local anesthetics, buffers and the like.

It can also be packaged in delay or progressive release forms.

The compound of formula (I) conforming to the present invention is generally present in the pharmaceutical compositions in an amount ranging from 0.01 to 20 weight percent relative to the total weight of the composition and preferably from 0.1 to 5 weight percent.

In a therapeutic use, the treatment is determined by the practioner and can vary according to the age, weight and patient response as well as to the seriousness of the symptoms.

When the compounds of formula (I) are administered orally, the dosage is generally between 0.1 and 50 mg/kg/day and preferably between 0.2 to 20 mg/kg/day. The duration of the treatment varies according to the seriousness of the symptoms and can extend between 1 and 25 weeks in a continuous or discontinuous fashion.

The topically applied compositions contain preferably from 0.25 to 4 weight percent of the compound of formula (I). As the support or excipient of the pharmaceutical composition according to the present invention, any conventional non-toxic support or excipient can be employed.

In order to illustrate the invention and without any limiting character, examples of the preparation of the compounds of formula (I) as well as examples of the use of these compounds in the cosmetic and pharmaceutical fields are now given.

EXAMPLE I

Preparation of
4-methoxy-5,5,8,8-tetramethyl-5,6,7,8-tetrahydro-1-naphthalenol (a) 2,5-dichloro-2,5-dimethyl hexane A suspension of 14.6 g of 2,5-dimethyl-2,5-hexanediol in 150 cm$^3$ of concentrated HCl is stirred, for 1 hour, at a temperature of about 5° C. The solid is then filtered, thoroughly washed with water and then dried at ambient temperature on potash and under reduced pressure. 16.5 g of 2,5-dichloro-2,5-dimethyl hexane in the form of white crystals melting at 65° C. are obtained.

(b) 4-methoxy-5,5,8,8-tetramethyl-5,6,7,8-tetrahydro-1-naphthalenol

At a temperature between 0° and 5° C., under an inert atmosphere, 10.8 g of anhydrous aluminum chloride are added to a suspension of 49.7 g of 4-hydroxy anisole and 73.2 g of 2,5-dichloro-2,5-dimethyl hexane, obtained in step (a) above, in 230 cm$^3$ of 1,2-dichloroethane.

5 minutes after the introduction of the aluminum chloride, the medium becomes homogeneous and is progressively colored red-brown. This mixture is then stirred for 5 hours at ambient temperature, at the end of which time the major portion of the initial reactant is transformed. 200 cm$^3$ of ice water are then added. The mixture is stirred for ¼ hour, then the phase is decanted. The aqueous phase is extracted twice with 150 cm$^3$ of methylene chloride. The combined organic phases are washed with water, dried on sodium sulfate and the solvent is evaporated under reduced pressure. The crude product is then recrystallized in hexane. 50 g of 4-methoxy-5,5,8,8-tetramethyl-5,6,7,8-tetrahydro-1-naphthalenol are obtained in the form of white crystals having a melting point of 127° C.

| Elemental analysis: $C_{15}H_{22}O_2$ | | | |
|---|---|---|---|
| Calc.: | C: 76.88 | H: 9.36 | O: 13.65 |
| Found: | 76.87 | 9.50 | 13.73 |

EXAMPLE II

Preparation of
2-acetyl-4-methoxy-5,5,8,8-tetramethyl-5,6,7,8-tetrahydro-1-naphthalenol To a mixture, stirred under an inert atmosphere, at a temperature between 0° C. and 5° C., of 20.4 g of 4-methoxy-5,5,8,8-tetramethyl-5,6,7,8-tetrahydro-1-naphthalenol, obtained in Example I, and 6.18 cm, of acetyl chloride in 80 cm, of 1,2dichloroethane, there are added, by small portions, 17.4 g of anhydrous aluminum chloride over a period of about ½ hour in a manner so that the temperature does not exceed 5° C. At the end of the introduction the mixture is again stirred for 1 hour at this temperature and then for 1 hour at ambient temperature. The solution is then poured into 100 cm$^3$ of ice water. At this stage an emulsion is obtained which is extracted three times with 100 cm$^3$ of methylene chloride. The organic phases are combined, washed with water until a neutral pH of the wash waters, dried on sodium sulfate and the solvent removed by evaporation under a vacuum.

The resulting crude product is purified by silica gel chromatography. The anticipated acyl derivative is eluted with a 60/40 hexane/methylene chloride mixture. After evaporation of the eluant phases, then recrystallization in ethanol, 12 g of 2-acetyl-4-methoxy-5,5,8,8-tetramethyl-5,6,7,8-tetrahydro-1naphthalene are obtained in the form of light yellow needles having a melting point of 90° C.

| Elemental analysis: $C_{17}H_{24}O_3$ | | | |
|---|---|---|---|
| Calc.: | C: 73.88 | H: 8.75 | O: 17.37 |
| Found: | 73.87 | 8.84 | 17.20 |

In the last chromatography fractions a secondary product is entrained which corresponds to an O-acylation. It is a question of 1-acetoxy-4-methoxy-5,5,8,8-tetramethyl-5,6,7,8-tetrahydro naphthalene in the form of white crystals having a melting point of 90° C.

EXAMPLE III

Preparation of
2-(1-hydroxyethyl)-4-methoxy-5,5,8,8-tetramethyl-5,6,7,8-tetrahydro-1-naphthelenol To a stirred solution at ambient temperature under inert atmosphere, of 2.9 g of 2-acetyl-4-methoxy-5,5,8,8-tetramethyl-5,6,7,8-tetrahydro-1-naphthalenol, obtained in Example II, in a mixture of 40 cm$^3$ of methanol and 5 cm$^3$ of tetrahydrofuran, there are added over a period of about 20 minutes, by small portions, 1.5 g of sodium borohydride. After the end of the introduction the solution is again stirred for 1 hour at ambient temperature, then cooled to about 5° C., the temperature at which there are introduced, with stirring, 100 cm$^3$ of water. This mixture is acidified, with stirring, by the addition of 45 cm$^3$ of 1N HCl, then extracted 3 times with 50 cm$^3$ of ethyl ether. The ether phases are combined, washed with water, dried on sodium sulfate and then concentrated to dryness.

3 g of a yellow solid are obtained and then purified by passage through a silica gel column that is eluted with methylene chloride.

After evaporation of the eluant, 2.4 g of a light yellow powder having a melting point of 99° C. are obtained.

| Elemental analysis: $C_{17}H_{26}O_3$ | | | |
|---|---|---|---|
| Calculated: | C: 73.35 | H: 9.41 | O: 17.24 |
| Found: | 73.25 | 9.40 | 17.44 |

EXAMPLE IV

Preparation of
2-(2-hydroxy-2-propyl)-4-methoxy-5,5,8,8-tetramethyl-5,6,7,8-tetrahydro-1-naphthalenol To a stirred solution, at −25° C. under an inert atmosphere, of 7.3 g of 2-acetyl-4-methoxy-5,5,8,8-tetramethyl-5,6,7,8-tetrahydro-1-naphthalene, obtained in Example II, in 120 cm$^3$ of anhydrous ethyl ether, there are added over a period of about ¼ hour, 19 cm$^3$ of a 3M solution of methyl magnesium bromide in ether.

The formation of a yellow precipitate is observed and the temperature at the end of the introduction of the magnesium is −15° C. Stirring is maintained for an additional ½ hour at this temperature, then for 1 hour at 10° C. The major portion of the initial reactant is thus transformed. The mixture is hydrolyzed at 0° C. by the addition of 25 cm$^3$ of water, then 60 cm$^3$ of 1N HCl. The ether phase is decanted and the aqueous phase extracted twice with 100 cm$^3$ of ethyl ether.

The combined organic phases are washed with water, dried on sodium sulfate and concentrated. The resulting white solid is recrystallized in hexane in the presence of a trace of acetone. 7 g of 2-(2-hydroxy-2-propyl)-4-methoxy-5,5,8,8-tetramethyl-5,6,7,8 -tetrahydro-1-naphthalenol are obtained in the form of white crystals having a melting point of 140° C.

| Elemental analysis: C$_{18}$H$_{28}$O$_3$ | | | |
|---|---|---|---|
| Calculated: | C: 73.93 | H: 9.65 | O: 16.41 |
| Found: | 74.02 | 9.62 | 16.30 |

EXAMPLE V

Preparation of
2-(2-propenyl)-4-methoxy-5,5,8,8-tetramethyl-5,6,7,8-tetrahydro-1-naphthalenol At ambient temperature, 30 cm$^3$ of a 50% solution of sulfuric acid are slowly added to 2 g of 2-(2-hydroxy-2-propyl)-4-methoxy-5,5,8,8-tetramethyl-5,6,7,8-tetrahydro-1-naphthalenol, obtained in Example IV, dissolved in 30 cm$^3$ of methylene chloride. The mixture is left to stand overnight at ambient temperature. The methylene chloride phase is decanted, washed with water until neutral pH of the wash waters, dried on sodium sulfate and then concentrated. The expected product is purified by passage through a silica gel chromatography column. It is eluted by a 50:50 mixture of methylene chloride/hexane.

After evaporation of the eluant, 1.3 g of a light yellow liquid, whose NMR $^1$H 80 MHz spectrum corresponds to the expected structure, are obtained.

EXAMPLE VI

Preparation of
1-hydroxy-4-methoxy-5,5,8,8-tetramethyl-5,6,7,8-tetrahydro naphthalene carboxylic acid (a)
1,4-dimethoxy-5,5,8,8-tetramethyl-5,6,7,8-tetrahydro naphthalene To a solution, stirred at 0° C. under an inert atmosphere, of 165.5 g of 1,4-dimethoxybenzene and 218.7 g of 2,5dichloro-2,5 -dimethyl hexane, obtained in Example I(a), in 750 cm$^3$ of anhydrous 1,2-dichloroethane, there are added, all at once, 31.9 g of powdered anhydrous aluminum chloride. The mixture is stirred for 1 hour at ambient temperature and then left to stand overnight. The next day after 4 hours stirring at this temperature, 600 cm$^3$ of ice water are added. The organic phase is decanted and the aqueous phase is extracted three time with 400 cm$^3$ of methylene chloride. The organic phases are combined, washed with water until neutral pH of the wash waters, then dried on sodium sulfate and concentrated. The resulting crude product is treated with animal charcoal in boiling ethanol, then recrystallized in this solvent. 195 g of 1,4-dimethoxy-5,5,8,8-tetramethyl-5,6,7,8-tetrahydro naphthalene are obtained in the form of white needles having a melting point of 195° C.

(b)
2-acetyl-1,4-dimethoxy-5,5,8,8-tetramethyl-5,6,7,8-tetrahydro naphthalene

To a solution, stirred at a temperature of about -10° C., of 74. 4 g of 1,4-dimethoxy-5,5,8,8-tetramethyl-5,6,7,8-tetrahydro naphthalene, obtained in step (a) above, and 21.3 cm$^3$ of acetyl chloride in 380 cm$^3$ of 1,2-dichloroethane, there are added, in small portions, 48 g of anhydrous aluminum chloride over a period of about ¾ hour. After the end of the addition, the mixture is stirred for 1 hour 30 minutes at 0° C., and diluted by the addition of 700 cm$^3$ ice water. The organic phase is then decanted, washed several times with water until neutral pH of the wash waters and dried on sodium sulfate. After removal of the solvent by distillation under a vacuum, the resulting crude product is recrystallized in ethanol. 76 g of 2-acetyl-1,4-dimethoxy-5,5,8,8-tetramethyl-5,6,7,8-tetrahydro naphthalene are obtained in the form of white needles having a melting point of 97° C.

| Elemental analysis: C$_{18}$H$_{26}$O$_3$ | | | |
|---|---|---|---|
| Calculated: | C: 74.45 | H: 9.02 | O: 16.53 |
| Found: | 74.42 | 8.99 | 16.62 |

(c)
1,4-dimethoxy-5,5,8,8-tetramethyl-5,6,7,8-tetrahydro-2-naphthalene carboxylic acid In a first stage a sodium hypobromite solution is prepared by slowly adding 77 cm$^3$ of bromine to a solution containing 192.7 g of soda in 890 cm$^3$ water cooled to between 0° C. and 5° C. The mixture is kept, with stirring, at 0° C.

In a second stage, this hypobromite solution is slowly added to a stirred solution, cooled to about 5° C., of 43 g of 2-acetyl-1,4-dimethoxy-5,5,8,8-tetramethyl-5,6,7,8-tetrahydro naphthalene, obtained in stage (b) above, in 500 cm$^3$ of dioxane. The rate of introduction is such that the temperature does not exceed 15° C. The reaction mixture is then left to stand overnight, diluted with 300 cm$^3$ of water, then, at a temperature lower than 20° C., the excess sodium hypobromite is destroyed by the slow addition of a 25% aqueous solution of sodium bisulfite. The expected acid is then precipitated by acidifying the mixture by the addition of 380 cm$^3$ of 6N HCl. The precipitate is filtered, washed with water and dried under reduced pressure. 40.8 g of 1,4-dimethoxy-5,5,8,8-tetramethyl-5,6,7,8-tetrahydro-2-naphthalene carboxylic acid are obtained in the form of a white solid having a melting point of 187° C.

| Elemental analysis: C$_{17}$H$_{24}$O$_4$ | | | |
|---|---|---|---|
| Calculated: | C: 69.84 | H: 8.27 | O: 21.89 |
| Found: | 69.56 | 8.29 | 21.64 |

(d)
1-hydroxy-4-methoxy-5,5,8,8-tetramethyl-5,6,7,8-tetrahydro-2-naphthalene carboxylic acid To a stirred solution, at ambient temperature under an inert atmosphere, of 30 g of 1,4-dimethoxy-5,5,8,8-tetramethyl-5,6,7,8-tetrahydro-2-naphthalene carboxylic acid, obtained above in stage (c), in 150 cm$^3$ of acetic acid 300 cm$^3$ of a 57% solution of iodhydric acid are rapidly added. The mixture is then brought to reflux for ½ hour, then the temperature is adjusted towards 30° C., the temperature at which it is poured into 1250 cm³ of ice water. The precipitate which forms is filtered, washed several times with water until neutral pH of the wash waters and then dried.

27 g of 1-hydroxy-4-methoxy-5,5,8,8-tetramethyl-5,6,7,8-tetrahydro-2-naphthalene carboxylic acid containing a small amount of 1,4-dihydroxy-5,5,8,8-tetramethyl-5,6,7,8-tetrahydro-2-naphthalene carboxylic acid are obtained.

This mixture is fractionated by chromatography on a silica gel column. The principal product is eluted with a 2/8/90 acetic acid/dioxane/toluene mixture. After evaporation of the eluant and recrystallization in toluene 10 g of 1-hydroxy-4-methoxy-5,5,8,8-tetramethyl-5,6,7,8-tetrahydro-2-naphthalene carboxylic acid are obtained in the form of white crystals having a melting point of 213° C.

| Elemental analysis: $C_{16}H_{22}O_4$ | | | |
|---|---|---|---|
| Calculated: | C: 69.04 | H: 7.97 | O: 22.99 |
| Found | 69.14 | 8.01 | 23.08 |

In the following elution fractions, 1,4-dihydroxy-5,5,8,8-tetramethyl-5,6,7,8-tetrahydro-2-naphthalene carboxylic acid is entrained. After evaporation of the eluant, 3 g of beige crystals having a melting point of 215° C. are obtained.

| Elemental analysis: $C_{15}H_{20}O_4$ | | | |
|---|---|---|---|
| Calculated: | C: 68.16 | H: 7.63 | O: 24.21 |
| Found | 68.20 | 7.61 | 24.32 |

If it is desired to obtain this latter acid as the principal product then the reaction mixture is maintained at least 3 hours under reflux.

EXAMPLE VII

Preparation of 1,4-dihydroxy-5,5,8,8-tetramethyl-5,6,7,8-tetrahydro naphthalene (a) 5,5,8,8-tetramethyl-5,6,7,8-tetrahydro-1,4-naphthoquinone To a solution of 17.42 g (0.07 mole) of 1,4-dimethoxy-5,5,8,8-tetramethyl-5,6,7,8-tetrahydro naphthalene, obtained in Example VIa, in 340 cm³ of dioxane, cooled to +5° C., there are added, with stirring, 34.7 g (0.28 mole) of silver oxide, AgO(II), then rapidly drop-by-drop, 70 cm³ (0.42 mole) of 6N HNO₃.

Cooling is suspended and the reaction mixture is stirred until there is a total consumption of the silver oxide (10 to 15 minutes). 500 cm³ of dichloromethane in 200 cm³ of water are then added.

The organic phase is separated by decanting, washed with 200 cm³ of water, dried on sodium sulfate and evaporated to dryness. The resulting red oil is chromatographed on silica gel using, as the eluant, a 60/40 hexane/dichloromethane mixture.

After evaporation and drying 2.7 g of 5,5,8,8-tetramethyl-5,6,7,8-tetrahydro-1,4-naphthoquinone are obtained in the form of a red oil.

The NMR ¹H 80 MHz spectrum conforms to the expected structure.

| Elemental analysis: $C_{14}H_{18}O_2$ | | | |
|---|---|---|---|
| Calculated: | C: 77.03 | H: 8.31 | O: 14.66 |
| Found: | 76.87 | 8.28 | 14.68 |

(b) 1,4-dihydroxy-5,5,8,8-tetramethyl-5,6,7,8-tetrahydronaphthalene

To a suspension of 40 mg (~1 mole) of lithium aluminum hydride in 2 cm³ of anhydrous ethyl ether, stirred under an inert atmosphere and cooled to +5° C., there is slowly added a solution of 0.22 g (~1 mole) of 5,5,8,8-tetramethyl-5,6,7,8-tetrahydro-1,4-naphthoquinone, obtained in step (a) above, in 2 cm³ of anhydrous ethyl ether. After 30 minutes of stirring water is slowly added to destroy excess hydride, then 30 cm³ of ethyl ether and finally a few drops of 1N Hcl up to an acid pH.

The ether phase is separated, washed with water, dried on sodium sulfate and evaporated to dryness under an inert atmosphere.

0.2 g of 1,4-dihydroxy-5,5,8,8-tetramethyl-5,6,7,8-tetrahydro naphthalene is obtained in the form of a beige solid having a melting point of 114° C.

The NMR ¹H CDCl₃ 80 MHz spectrum under an inert atmosphere conforms to the expected structure ($\delta=1.25$ ppm, s, 12H; HCH₃; $\delta=164$ ppm, s, 4H, 2CH₂; $\delta=6.90$ ppm, 2H aromatics).

When the solution in deutrochloroform is not preserved under an inert gas there is observed the presence of stray signals corresponding to the quinone ($\delta=1.29$ ppm, s, CH₃:$\delta=1.51$ ppm, s, CH₂; H quinonics). After 5 hours in solution the quinone is no longer observed.

| Elemental analysis: $C_{14}H_{20}O_2$ | | | |
|---|---|---|---|
| Calculated: | C: 76.32 | H: 9.15 | O: 14.52 |
| Found: | 76.37 | 8.98 | 14.60 |

EXAMPLE VIII

Preparation of 2-benzoyl-4-methoxy-5,5,8,8-tetramethyl-5,6,7,8-tetrahydro-1-naphthalenol To a solution cooled to +5° C. of 23.44 g (0.1 mole) of 4-methoxy-5,5,8,8-tetramethyl-5,6,7,8-tetrahydro-1-naphthalenol, obtained in Example I, in 400 cm³ of anhydrous 1,2-dichloroethane and 11.7 cm³ (14.06 g=0.1 mole) of benzoyl chloride, there are added, by portions, 16 g (0.12 mole) of anhydrous aluminum chloride over a period of about 30 minutes.

At the end of the introduction, the mixture is stirred for 2 hours while permitting the temperature to return to ambient temperature.

The solution is then poured into 250 cm³ of ice water. The aqueous phase is separated by decanting and re-extracted 3 times with 200 cm³ of dichloromethane. The organic phases are combined, washed with water until a neutral pH of the wash waters, dried on sodium sulfate and evaporated to dryness under reduced pressure.

The resulting crude product (32.2 g) is purified by chromatography on silica gel with a 90/10 heptane/dichloromethane eluant.

After evaporation of the eluant phases, then drying under a vacuum at 60° C., 19.95 g of 2-benzoyl-4-methoxy-5,5,8,8-tetramethyl-5,6,7,8-tetrahydro-1-naphthalenol are obtained in the form of a yellow solid having a melting point of 85° C.

The NMR $^1$H 80 MHz spectrum conforms to the expected structure.

EXAMPLE IX

Preparation of 2-benzyl-4-methoxy-5,5,8,8-tetramethyl-5,6,7,8-tetrahydro-1-naphthalenol To a suspension of 30 mmoles of sodium hydride in 5 cm$^3$ of toluene, stirred at ambient temperature under an inert atmosphere, there is slowly added a solution of 7.22 g (30 mmoles) of 4-methoxy-5,5,8,8-tetramethyl-5,6,7,8-tetrahydro-1-naphthalenol, obtained in Example I, in about 20 cm$^3$ of toluene while maintaining the temperature at 20° C. The resulting solution is heated to reflux. 4.33 g (33.9 mmoles) of benzyl chloride are slowly introduced over a period of about 30 minutes. Reflux is maintained 5 hours. After cooling to ambient temperature 40 cm$^3$ of lN HCl are slowly added and the mixture is stirred for 15 minutes. The two phases are separated by decanting. The aqueous phase is re-extracted twice with 200 cm$^3$ of toluene. The organic phases are combined, washed with water, dried on sodium sulfate and concentrated under reduced pressure. The resulting oil is purified by silica gel chromatography using a 90/10 heptane/dichloromethane mixture as the eluant, followed by recrystallization in ethyl alcohol at 96° C.

After filtering and drying under a vacuum at 60° C. 2.2 g of 2-benzyl-4-methoxy-5,5,8,8-tetramethyl-5,6,7,8-tetrahydro-1-naphthalenol are obtained in the form of a white solid having a melting point of 80° C.

The NMR $^1$H 250 MHz spectrum conforms to the expected structure.

| Elemental analysis: $C_{22}H_{28}O_2$ | | | |
|---|---|---|---|
| Calculated: | C: 81.44 | H: 8.70 | O: 9.86 |
| Found | 81.48 | 8.63 | 10.03 |

EXAMPLES OF COMPOSITIONS

Example A

Gel

| | |
|---|---|
| 2-(1-hydroxyethyl)-4-methoxy-5,5,8,8-tetramethyl-5,6,7,8-tetrahydro-1-naphthalenol | 0.12 g |
| Carboxy vinyl polymer, sold by Goodrich under the trade name "Carbopol 934" | 0.80 g |
| Glycerine | 12.00 g |
| Ethanol | 15.00 g |
| Preservative | 0.20 g |
| Perfume | 0.20 g |
| Triethanolamine, sufficient for pH = 5.3 | |
| Demineralized water, sufficient amount for | 100.00 g |

Example B

Oil

| | |
|---|---|
| 4-methoxy-5,5,8,8-tetramethyl-5,6,7,8-tetrahydro-1-naphthalenol | 0.60 g |
| Benzoate of $C_{12}$-$C_{15}$ alcohols, sold by Finetex under the trade name "FINSOLV TN" | 30.00 g |
| Stabilized, raffinated turnsole oil | 20.00 g |
| Perfume | 1.00 g |
| Silicone oil, sold by Union Carbide under the trade name "Volatile silicone 7207", sufficient amount for | 100.00 g |

Example C

Milk in the Form of a Water-in-Oil Emulsion

| | |
|---|---|
| 2-(2-hydroxy-2-propyl)-4-methoxy-5,5,8,8-tetramethyl-5,6,7,8-tetrahydro-1-naphthalenol | 0.25 g |
| Benzylidene camphor | 2.00 g |
| Mixture of fatty acid esters, polyglycerolated esters and silicone surfactants, sold by Goldschmidt under the trade name "ABIL W SO 8" | 5.00 g |
| White petrolatum | 2.00 g |
| Beeswax | 2.50 g |
| Benzoate of $C_{12}$-$C_{15}$ alcohols, sold by Finetex under the trade name "FINSOLV TN" | 19.00 g |
| Glycerine | 5.00 g |
| Sodium chloride | 2.00 g |
| Perfume | 0.40 g |
| Preservative | 0.20 g |
| Demineralized water, sufficient amount for | 100.00 g |

Example D

Milk

| | |
|---|---|
| 2-(1-hydroxyethyl)-4-methoxy-5,5,8,8-tetramethyl-5,6,7,8-tetrahydro-1-naphthalenol | 1.50 g |
| 2-ethylhexyl p-hydroxycinnamate, sunscreen agent | 3.50 g |
| 2-hydroxy-4-methoxy benzophenone, sunscreen agent | 1.00 g |
| Cetyl alcohol | 1.00 g |
| Oleocetyl alcohol having 30 moles of ethylene oxide, sold by Henkel under the trade name "MERGITAL OC 30" | 5.00 g |
| Stearyl alcohol | 4.00 g |
| 1-hexadecanoyloxy-3-(2'-ethyl hexyl ether)-2-propanol | 2.00 g |
| 90/10 mixture of ketostearyl 2-ethyl hexanoate and isopropyl myristate, sold under the trade name "CERAMOLL" by Creations Aromatiques | 2.00 g |
| Petrolatum oil | 8.00 g |
| Propylene glycol | 8.00 g |
| Preservative | 0.20 g |
| Perfume | 0.40 g |
| Demineralized water, sufficent amount for | 100.00 g |

Example E

Stick

| | |
|---|---|
| 4-methoxy-5,5,8,8-tetramethyl-5,6,7,8-tetrahydro-1-naphthalenol | 1.00 g |
| Ozokerite | 20.00 g |
| Beeswax | 7.00 g |
| Oleic alcohol | 12.00 g |
| Hydrogenated lanolin | 8.00 g |
| Lanolin oil | 8.00 g |
| Carnauba wax | 1.00 g |
| Benzoate of $C_{12}$-$C_{15}$ alcohols, sold by Finetex under the trade name "FINSOLV TN" | 17.00 g |
| Octamethylcyclotetrasiloxane, sold by Goldschmidt under the trade name "ABIL K4" | 3.00 g |
| Petrolatum oil, sufficient amount for | 100.00 g |

Example F

Cream in the Form of an Oil-in-Water Emulsion

| | |
|---|---|
| 2-(1-hydroxyethyl)-4-methoxy-5,5,8,8-tetramethyl-5,6,7,8-tetrahydro-1-naphthalenol | 0.50 g |
| (2-oxo-3-bornylidene)-4-methyl phenyl trimethyl ammonium methyl sulfate | 4.00 g |
| Sodium lactate | 1.00 g |
| Keto-stearyl alcohol and oxyethylenated fatty alcohols, sold by Sinnova under the trade name "SINNOWAX 40" | 7.50 g |
| Mixture of non self-emulsifiable glycerol mono and distearate | 2.0 g |
| Cetyl alcohol | 1.00 g |
| Myristic alcohol | 0.60 g |
| Sorbitol, 70% | 3.00 g |
| Isopropyl palmitate | 10.00 g |
| Petrolatum oil | 7.00 g |
| Preservative | 0.20 g |
| Perfume | 0.60 g |
| Demineralized water, sufficient amount for Pharmaceutical Composition For Topical Application | 100.00 g |

Example G

Ointment

| | |
|---|---|
| 4-methoxy-5,5,8,8-tetramethyl-5,6,7,8-tetrahydro-1-naphthalenol | 2.00 g |
| Fluid petrolatum oil | 9.10 g |
| Silica, sold by Degussa under the trade name "AEROSIL 200" | 9.20 g |
| Isopropyl myristate, sufficient amount for | 100.00 g |

In this example the active compound can be replaced by the same amount of 2-benzyl-4-methoxy-5,5,8,8-tetramethyl-5,6,7,8-tetrahydro-1-naphthalenol.

Example H

Anionic Oil-in-Water Cream

| | |
|---|---|
| 2-(1-hydroxyethyl)-4-methoxy-5,5,8,8-tetramethyl-5,6,7,8-tetrahydro-1-naphthalenol | 3.00 g |
| Sodium dodecyl sulfate | 0.80 g |
| Glycerol | 2.00 g |
| Stearyl alcohol | 20.00 g |
| Triglycerides of capric/caprylic acids, sold by Dynamit Nobel under the trade name "MIGLYOL 812" | 20.00 g |
| Preservative, sufficient amount | |
| Demineralized water, sufficient amount for | 100 g |

In this example the active compound can be replaced by the same amount of 2-benzyl-4-methoxy-5,5,8,8-tetramethyl-5,6,7,8-tetrahydro-1-naphthalenol.

Example I

Gel

| | |
|---|---|
| 2-(2-hydroxy-2-propyl)-4-methoxy-5,5,8,8-tetramethyl-5,6,7,8-tetrahydro-1-naphthalenol | 1.00 g |
| Hydroxypropyl cellulose, sold by Hercules under the trade name "KLUCEL HF" | 2.00 g |
| Ethanol | 70.00 g |
| Water, sufficient amount for | 100.00 g |

In this example the active compound can be replaced by 0.5 g of 2-benzyl-4-methoxy-5,5,8,8-tetramethyl-5,6,7,8-tetrahydro-1-naphthalenol.

What is claimed is:

1. A cosmetic composition for the protection of human skin or hair comprising in a cosmetically acceptable support containing at least one oily phase, at least one 5,6,7,8-tetrahydro-1-naphthalenol derivative having the formula

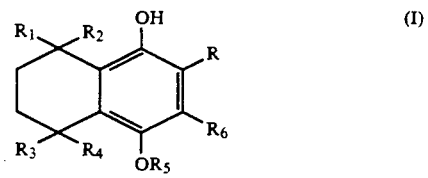

wherein $R_1$, $R_2$, $R_3$ and $R_4$ represent lower alkyl, $R_5$ and $R_6$ represent hydrogen or lower alkyl, R represents hydrogen, $C_1$–$C_{18}$ alkyl, $C_2$–$C_{18}$ alkyl substituted by one or more hydroxy groups, $C_3$–$C_{18}$ alkenyl, $C_2$–$C_{18}$ acyl, benzyl, benzoyl, carboxyl and the carboxylic salts of an alkali or alkaline earth metal or of an organic amine, said derivative being present in an amount effective to protect said human skin or hair.

2. The cosmetic composition of claim 1 wherein said compound of formula I is selected from the group consisting of 4-methoxy-5,5,8,8-tetramethyl-5,6,7,8-tetrahydro-1-naphthalenol, 2-acetyl-4-methoxy-5,5,8,8-tetramethyl-5,6,7,8-tetrahydro-1-naphthalenol, 2-(1-hydroxyethyl)-4-methoxy-5,5,8,8-tetramethyl-5,6,7,8-tetrahydro-1-naphthalenol, 2-(2-hydroxy-2-propyl)-4-methoxy-5,5,8,8-tetramethyl-5,6,7,8-tetrahydro-1-naphthalenol, 2-(2-propenyl)-4-methoxy-5,5,8,8-tetramethyl-5,6,7,8-tetrahydro-1-naphthalenol, 1-hydroxy-4-methoxy-5,5,8,8-tetramethyl-5,6,7,8-tetrahydro naphthalene carboxylic acid, 1,4-dihydroxy-5,5,8,8-tetramethyl-5,6,7,8-tetrahydro naphthalene, 2-benzoyl-4-methoxy-5,5,8,8-tetramethyl-5,6,7,8-tetrahydro-1-naphthalenol and 2-benzyl-4-methoxy-5,5,8,8-tetramethyl-5,6,7,8-tetrahydro-1-naphthalenol.

3. The cosmetic composition of claim 1 wherein said compound of formula I is present in an amount ranging from 0.05 to 10 percent by weight based on the total weight of said composition.

4. A pharmaceutical composition for avoiding peroxidation of cutaneous lipids comprising in a pharmaceutically acceptable support or excipient at least one 5,6,7,8-tetrahydro-1-naphthalenol derivative having the formula

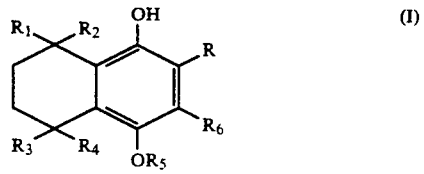

wherein $R_1$, $R_2$, $R_3$ and $R_4$ represent lower alkyl, $R_5$ and $R_6$ represent hydrogen or lower alkyl, R represents hydrogen, $C_1$–$C_{18}$ alkyl, $C_2$–$C_{18}$ alkyl substituted by one or more hydroxy groups, $C_3$–$C_{18}$ alkenyl, $C_2$–$C_{18}$ acyl, benzyl, benzoyl, carboxyl and the carboxylic salts of an alkali or alkaline earth metal or of an organic amine, said derivative being present in an amount sufficient to avoid peroxidation of cutaneous lipids.

5. The pharmaceutical composition of claim 4 wherein said compound of formula I is present in an amount ranging from 0.01 to 20 percent by weight based on the total weight of said composition.

6. The pharmaceutical composition of claim 4 wherein said compound of formula I is present in an amount ranging from 0.1 to 5 percent by weight based on the total weight of said composition.

7. The pharmaceutical composition of claim 4 wherein said compound of formula I is selected from the group consisting of 4-methoxy-5,5,8,8-tetramethyl-5,6,7,8-tetrahydro-1-naphthalenol, 2-acetyl-4-methoxy-5,5,8,8-tetramethyl-5,6,7,8-tetrahydro-1-naphthalenol, 2-(1-hydroxyethyl)-4-methoxy-5,5,8,8-tetramethyl-5,6,7,8-tetrahydro-1-naphthalenol, 2-(2-hydroxy-2-propyl)-4-methoxy-5,5,8,8-tetramethyl-5,6,7,8-tetrahydro-1-naphthalenol, 2-(2-propenyl)-4-methoxy-5,5,8,8-tetramethyl-5,6,7,8-tetrahydro-1-naphthalenol, 1-hydroxy-4-methoxy-5,5,8,8-tetramethyl-5,6,7,8-tetrahydro naphthalene carboxylic acid, 1,4-dihydroxy-5,5,8,8-tetramethyl-5,6,7,8-tetrahydro naphthalene, 2-benzoyl-4-methoxy-5,5,8,8-tetramethyl-5,6,7,8-tetrahydro-1naphthalenol and -benzyl-4-methoxy-5,5,8,8-tetramethyl-5,6,7,8-tetrahydro-1naphthalenol.

8. A process for the preventative treatment of cutaneous inflammations and allergies comprising applying to the skin in an amount effective to prevent cutaneous inflammations and allergies the pharmaceutical composition of claim 4.

9. A process for protecting a cosmetic composition against oxidation comprising incorporating into said cosmetic composition at least one 5,6,7,8-tetrahydro-1-naphthalenol derivative having the formula (I)

wherein $R_1$, $R_2$, $R_3$ and $R_4$ represent lower alkyl, $R_5$ and $R_6$ represent hydrogen or lower alkyl, R represents hydrogen, $C_1$–$C_{18}$ alkyl, $C_2$–$C_{18}$ alkyl substituted by one or more hydroxy groups, $C_3$–$C_{18}$ alkenyl, $C_2$–$C_{18}$ acyl, benzyl, benzoyl, carboxyl and the carboxylic salts of an alkali or alkaline earth metal or of an organic amine, in an amount effective to protect said cosmetic composition against oxidation.

* * * * *